(12) United States Patent
Neelapu et al.

(10) Patent No.: US 10,699,415 B2
(45) Date of Patent: Jun. 30, 2020

(54) METHOD AND SYSTEM FOR AUTOMATIC VOLUMETRIC-SEGMENTATION OF HUMAN UPPER RESPIRATORY TRACT

(71) Applicant: Council of Scientific & Industrial Research, New Delhi (IN)

(72) Inventors: Bala Chakravarthy Neelapu, Chandigarh (IN); Harish Kumar Sardana, Chandigarh (IN); Om Prakash Kharbanda, New Delhi (IN); Viren Sardana, Chandigarh (IN); Abhishek Gupta, Chandigarh (IN); Srikanth Vasamsetti, Chandigarh (IN)

(73) Assignee: COUNCIL OF SCIENTIFIC & INDUSTRIAL RESEARCH (IN)

( * ) Notice: Subject to any disclaimer, the term of this patent is extended or adjusted under 35 U.S.C. 154(b) by 89 days.

(21) Appl. No.: 16/118,088

(22) Filed: Aug. 30, 2018

(65) Prior Publication Data

US 2019/0066303 A1 Feb. 28, 2019

(30) Foreign Application Priority Data

Aug. 31, 2017 (IN) .............................. 201711030803

(51) Int. Cl.
*G06T 7/11* (2017.01)
*G06T 7/155* (2017.01)
(Continued)

(52) U.S. Cl.
CPC .............. *G06T 7/11* (2017.01); *A61B 5/4818* (2013.01); *A61B 6/032* (2013.01); *A61B 6/469* (2013.01);
(Continued)

(58) Field of Classification Search
None
See application file for complete search history.

(56) References Cited

U.S. PATENT DOCUMENTS 7,787,673 B2 8/2010 Vaz et al.
7,835,555 B2 11/2010 Kiraly et al.
(Continued)

OTHER PUBLICATIONS

Shi, H., Scarfe, W.C. & Farman, A.G. Int J CARS (2006) 1: 83. https://doi.org/10.1007/s11548-006-0041 (Year: 2006).*
(Continued)

*Primary Examiner* — Tahmina N Ansari
(74) *Attorney, Agent, or Firm* — The Belles Group, P.C.

(57) ABSTRACT

Described herein is a method detecting a plurality of upper respiratory tract sub-regions automatically. Volume of interest (VOI) is identified based on the extraction of certain features, such as regional properties and shape-based features. The complete airway volume from a patient's data is identified by observing the area and eccentricity profiles of the certain volume/organ in the skull. Maxillary sinus area and eccentricity profile in the sagittal view is chosen in the present subject matter for level 1 VOI identification. Once a level 1 VOI is identified, the other sub-regions existing in the same VOI are further identified as individual level 2 VOI. Level 3 VOI is extracted based on the shape and geometric features of the organ. The extracted level 3 VOI is considered as the active contour that is followed by the initialized contour for the accurate segmentation of upper airway sub-regions.

18 Claims, 17 Drawing Sheets

(51) Int. Cl.
| | |
|---|---|
| *A61B 6/00* | (2006.01) |
| *G06T 7/00* | (2017.01) |
| *G06T 7/149* | (2017.01) |
| *G06T 7/136* | (2017.01) |
| *G06T 7/174* | (2017.01) |
| *A61B 5/00* | (2006.01) |
| *A61B 6/03* | (2006.01) |
| *G06T 7/12* | (2017.01) |

(52) U.S. Cl.
CPC ............ *A61B 6/501* (2013.01); *A61B 6/5217* (2013.01); *A61B 6/5223* (2013.01); *G06T 7/0012* (2013.01); *G06T 7/12* (2017.01); *G06T 7/136* (2017.01); *G06T 7/149* (2017.01); *G06T 7/155* (2017.01); *G06T 7/174* (2017.01); *G06T 2207/10081* (2013.01); *G06T 2207/20004* (2013.01); *G06T 2207/20116* (2013.01); *G06T 2207/20132* (2013.01); *G06T 2207/30008* (2013.01); *G06T 2207/30036* (2013.01)

(56) References Cited

U.S. PATENT DOCUMENTS

| | | |
|---|---|---|
| 8,050,470 B2 | 11/2011 | Coenen et al. |
| 2005/0207630 A1* | 9/2005 | Chan ..................... A61B 6/466 382/131 |
| 2010/0296718 A1* | 11/2010 | Ostrovsky-Berman ..................... G06T 7/187 382/133 |
| 2011/0293156 A1 | 12/2011 | Hsiao et al. |
| 2011/0311116 A1 | 12/2011 | Benn |
| 2014/0330115 A1* | 11/2014 | Schildkraut .......... A61B 6/5217 600/425 |
| 2019/0066303 A1* | 2/2019 | Neelapu .................. G06T 7/155 |

OTHER PUBLICATIONS

Solem et al., Three-dimensional soft-tissue and hard-tissue changes in the treatment of bimaxillary protrusion, American Journal of Orthodontics and Dentofacial Orthopedics, vol. 144, Issue 2, Aug. 2013, pp. 218-228, https://doi.org/10.1016/j.ajodo.2013.03.018 (Year: 2013).*

Neelapu, B.C., Kharbanda, O.P., Sardana, V. et al. Int J CARS (2017) 12: 1877. https://doi.org/10.1007/s11548-017-1650-1 (Year: 2017).*

* cited by examiner

| Regions | Landmarks | Volume cropping criteria | | Contour extraction |
|---|---|---|---|---|
| | | Limits | Anatomical definitions for the extraction of region of interest | |
| Region 1 | Nasion | Anterior | - | Extraction of contour by collecting the most anteriorly placed bony landmarks on the cropped region |
| | | Posterior | Line perpendicular to FH (Frankfort Horizontal) plane passing through PNS in sagittal view | |
| | | Upper | - | |
| | | Lower | line parallel to FH plane passing through PNS, in sagittal view | |
| Region 2 | Landmarks of Cervical bone | Anterior | Line perpendicular to FH plane passing through PNS in sagittal view | Extraction of corners of the disconnected components in cropped region |
| | | Posterior | - | |
| | | Upper | line parallel to FH plane passing through PNS, in sagittal view | |
| | | Lower | - | |
| Region 3 | ANS<br>A point<br>B point<br>Pogonion<br>Gnathion<br>Menton | Anterior | - | Extraction of contour by collecting the most anteriorly placed bony landmarks on the cropped region |
| | | Posterior | Line perpendicular to FH plane passing through PNS in sagittal view | |
| | | Upper | line parallel to FH plane passing through PNS, in sagittal view | |
| | | Lower | - | |
| Region 4 | Sella | Anterior | Line perpendicular to FH plane passing through PNS in sagittal view | Extraction of contour by collecting the most superiorly placed bony landmarks on the cropped region |
| | | Posterior | - | |
| | | Upper | - | |
| | | Lower | line parallel to FH plane passing through PNS, in sagittal view | |

FIG. 4

METHOD AND SYSTEM FOR AUTOMATIC VOLUMETRIC-SEGMENTATION OF HUMAN UPPER RESPIRATORY TRACT

CROSS-REFERENCE TO RELATED APPLICATIONS

This application claims the benefit of Indian Application No. 201711030803, filed Aug. 31, 2017. The disclosure of the above application is incorporated herein by reference.

FIELD OF THE INVENTION

The present disclosure relates to a method and system for automatic-segmentation of upper respiratory tract and its sub-regions.

BACKGROUND OF THE INVENTION

Orthodontic surgeons and Otorhinolaryngologists are known to analyze the patient's upper airway-volume. There are many clinical applications for the evaluation of the upper airway volumetric analysis, such as diagnosis of obstructive sleep apnea, evaluation of sinus anatomy, and dento-maxillofacial morphology in cephalometric analysis etc. Obstruction of upper airway leads to obstructive sleep apnea (OSA). Segmentation of upper airway volume helps to identify the region of obstruction and volumetric measurements of the segmented data for further analysis and surgery.

Conventionally, X-ray radiographs were used for the evaluation of airway anatomy. The airway analysis is performed based on the various linear and angular measurements made on the lateral X-ray films. This analysis is performed without calculating true volume, which is not appropriate for the clinical diagnosis and therefore treatment planning likely not to be significantly effective due to probable error in volume analysis. The evolution of CT/CBCT has made possible to visualize the true volume of airway. Eventually, segmentation of the desired volume becomes possible manually.

There are a host of manual/semi-automatic segmentation techniques available such as region growing, fixed thresholding, interactive thresholding etc. These techniques require a high level of human interventions, time and efforts, and are also dependent on human perception and experience. It makes the segmentation tedious for the observer and raises a need for automation.

OBJECTS OF THE INVENTION

The main objective of this present subject matter is to provide a method of automatic segmentation of upper airway and paranasal air sinuses which comprise of Oropharynx, Nasopharynx, Hypo-pharynx, Nasal Cavity, Maxillary air sinus, Frontal air sinus, Sphenoidal air sinus, and Ethmoidal air sinus.

Another objective of present subject matter is to provide a method of segmentation for measuring volume separately for various sub regions of human upper airway and paranasal air sinuses.

Yet another objective is to provide a method for automatic segmentation of each volume of human upper airway and paranasal air sinuses for visualization.

Yet another objective is to provide a robust method of segmentation, which will be applicable for patients of all classes of malocclusion.

SUMMARY OF THE INVENTION

This summary is provided to introduce a selection of concepts in a simplified-format that are further described in the detailed description of the present subject matter. This summary is not intended to identify key or essential inventive concepts of the present subject matter, nor is it intended for determining the scope of the present subject matter.

The present subject matter fully automatic segmentation of upper respiratory tract. Paranasal air sinuses include different airways surrounded by different bones, such as maxillary, ethmoidal, frontal, and sphenoid. The upper airway comprises of Nasal cavity, Nasopharynx, Oropharynx and Hypopharynx. The present subject matter is based on the anatomical knowledge. It's a rule based approach, whereas the rules are based on the knowledge of human anatomy. To detect the accurate volume, three levels of VOI by reducing volume further in each level, are used in this present subject matter. The initial segmentation of hard/soft tissue is performed by adaptive thresholding. The extraction of first level of volume of interest (VOI) is based on the anatomical boundary definitions of sub-regions. The requirement for level-2 VOI extraction is to detect certain landmarks based on the boundary-definitions. Automatic landmark detection is prior step to volume cropping and based on the anatomical-knowledge. The initial landmark is detected based on the geometrical and shape based feature extraction of a certain volume (e.g. maxillary sinus). From the initial detected landmark, anatomical definitions are used to detect the volume of interest (for landmark detection). Three-dimensional morphological operators, different geometrical shape based features and anatomical knowledge are used for further classification of the upper airway and paranasal sinus. The classified mask (level-3 VOI) is treated as the initialized contour for the level set segmentation algorithm. The volumetric analysis of these sub-regions is helpful in orthodontic practice for the proper diagnosis of obstructive sleep apnea, performing endoscopic surgery and the observation of treatment outcomes.

To further clarify advantages and features of the present subject matter, a more particular description of the present subject matter will be rendered by reference to specific embodiments thereof, which is illustrated in the appended drawings. It is appreciated that these drawings depict only typical embodiments of the present subject matter and are therefore not to be considered limiting of its scope. The present subject matter will be described and explained with additional specificity and detail with the accompanying drawings.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein:

FIG. 4 illustrates example definitions to detect landmarks for the selection of level 2 VOI, in accordance with an embodiment of the present subject matter;

Figure 1:
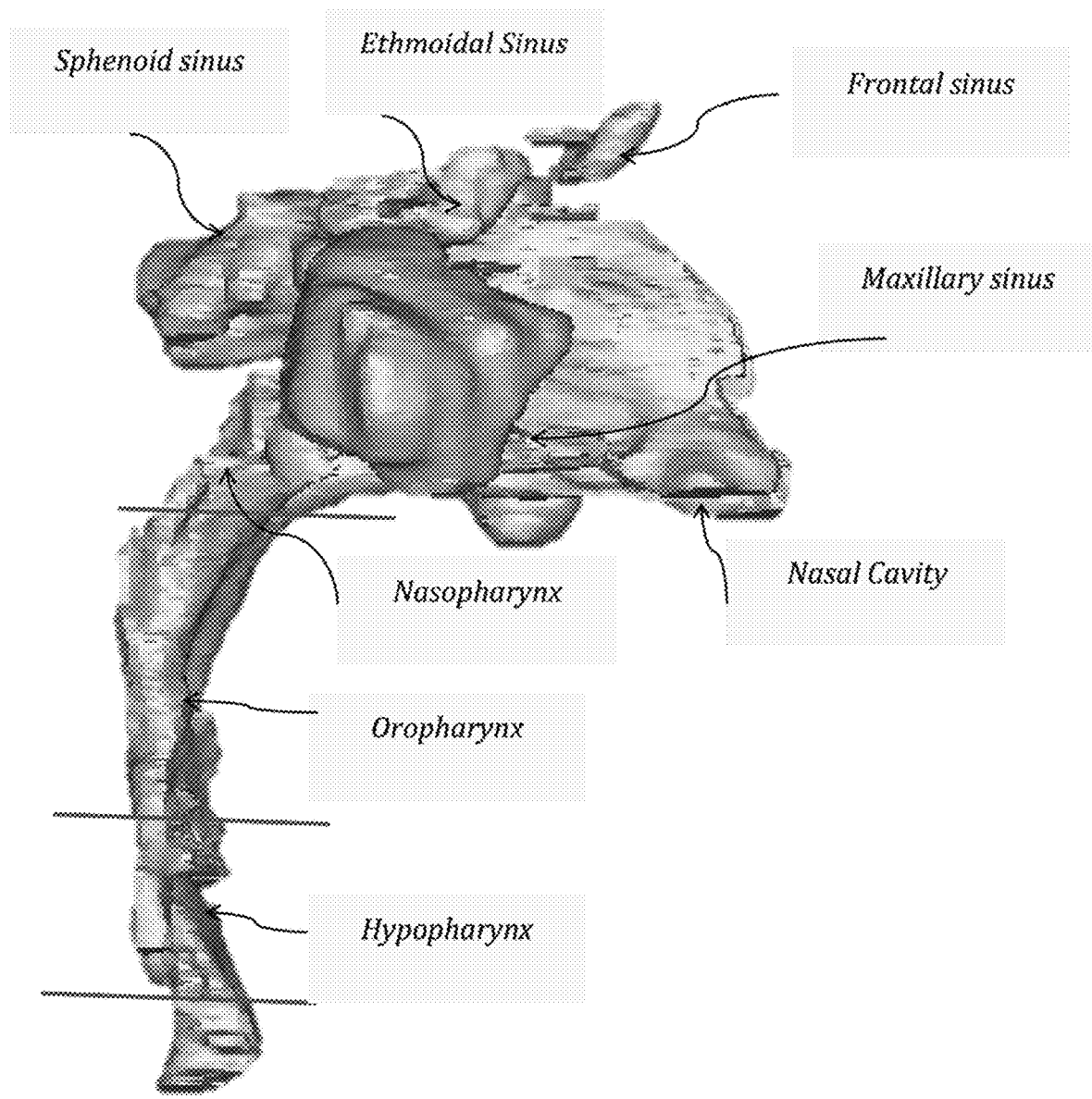
FIG. 1 illustrates an example upper airway volume segmented from the volumetric data, in accordance with an embodiment of the present subject matter.

Further, skilled artisans will appreciate that elements in the drawings are illustrated for simplicity and may not have been necessarily been drawn to scale. For example, the flow charts illustrate the method in terms of the most prominent steps involved to help to improve understanding of aspects of the present subject matter. Furthermore, in terms of the construction of the device, one or more components of the device may have been represented in the drawings by conventional symbols, and the drawings may show only those specific details that are pertinent to understand the embodiments of the present subject matter so as not to obscure the drawings with details that will be readily apparent to those of ordinary skill in the art having benefit of the description herein.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

For the purpose of promoting an understanding of the principles of the present subject matter, reference will now be made to the embodiment illustrated in the drawings and specific language will be used to describe the same. It will nevertheless be understood that no limitation of the scope of the present subject matter is thereby intended, such alterations and further modifications in the illustrated system, and such further applications of the principles of the present subject matter as illustrated therein being contemplated as would normally occur to one skilled in the art to which the present subject matter relates.

It will be understood by those skilled in the art that the foregoing general description and the following detailed description are explanatory of the present subject matter and are not intended to be restrictive thereof.

Reference throughout this specification to "an aspect", "another aspect" or similar language means that a particular feature, structure, or characteristic described in connection with the embodiment is included in at least one embodiment of the present subject matter. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures or components proceeded by "comprises . . . a" does not, without more constraints, preclude the existence of other devices or other sub-systems or other elements or other structures or other components or additional devices or additional sub-systems or additional elements or additional structures or additional components.

Unless otherwise defined, all technical and scientific terms used herein have the same meaning as commonly understood by one of ordinary skill in the art to which this present subject matter belongs. The system, methods, and examples provided herein are illustrative only and not intended to be limiting.

Embodiments of the present subject matter will be described below in detail with reference to the accompanying drawings.

A human upper respiratory tract comprises of paranasal air sinuses, nasal cavity and pharyngeal airway. Paranasal air sinus comprises of sub regions such as bilateral maxillary, ethmoidal, frontal sinuses and sphenoid sinus, and similarly, pharyngeal region comprises of Nasopharynx, Oropharynx and Hypopharynx.

FIG. 1 illustrates example human upper airway volume segmented as per the embodiment of the method presented.

The segmentation of these sub regions are performed by using level set active contour segmentation method. Contour initialization and identification of VOI (volume of interest) is the initial step of active contour segmentation. The contour can be initialized automatically or manually. Automatic initialization of contour is the challenging task in volumetric segmentation and this problem is solved in this present subject matter. An approach has been disclosed for the identification of separate VOI for each of the sub-regions of human upper airway. These VOIs are used to initialize the contour for the segmentation of desired volume using active contour segmentation method. The initialized contour converges/diverges towards boundaries depending upon the energy associated with the object boundaries. Hence, volume of each of the sub-regions of human upper airway can be detected. The approach disclosed in this present subject matter is not limited to use it for human upper airway. It can also be used for the segmentation of other volumetric regions.

The present subject matter for the automatic volumetric segmentation is described in following processing steps.

Figure 2:
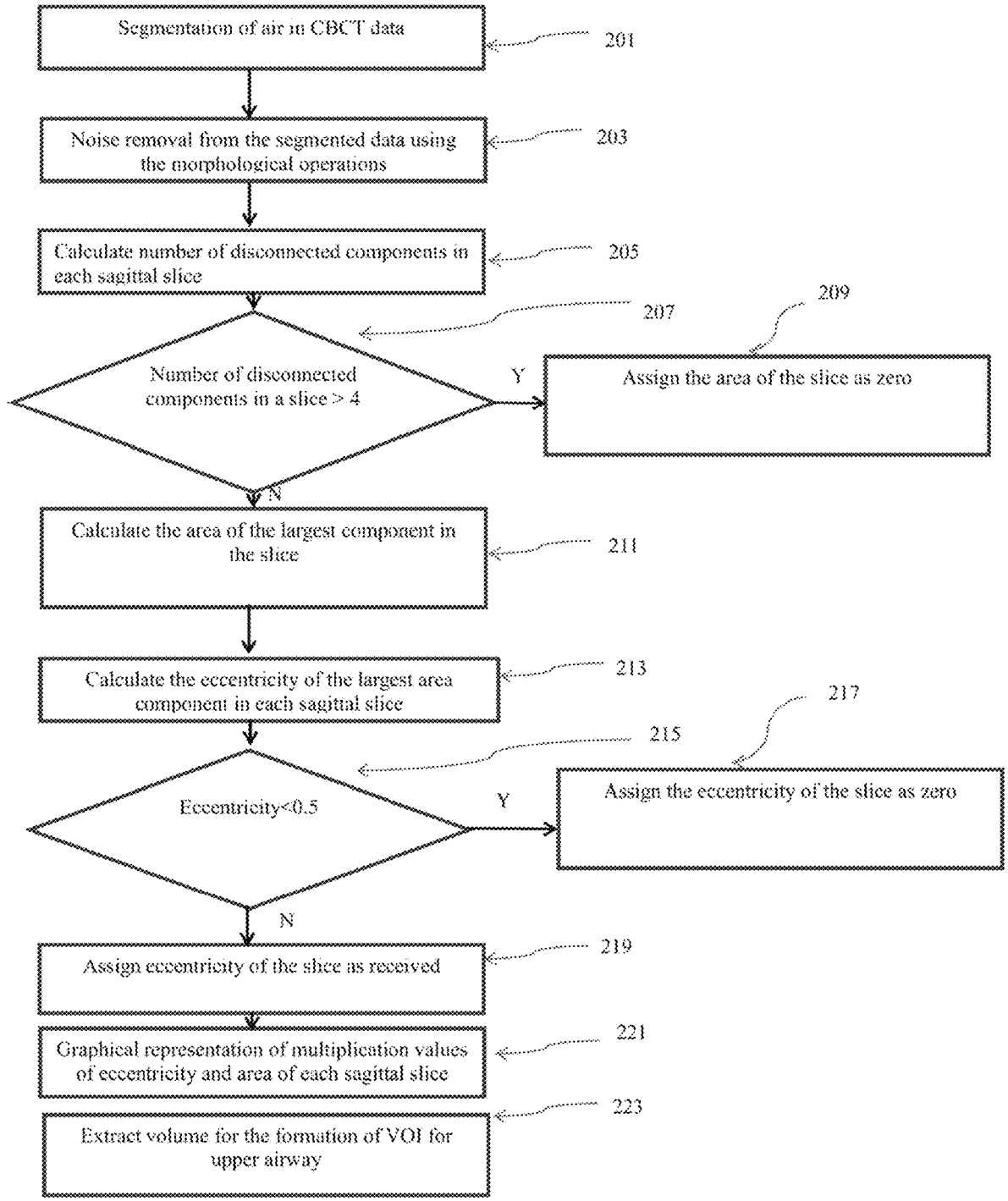
FIG. 2 illustrates a method for computing the area and eccentricity profile of the maxillary sinus in sagittal view of the volumetric data, in accordance with an embodiment of the present subject matter.

FIG. 2 illustrates a method for computing the area and eccentricity profile of the maxillary sinus in sagittal view of the volumetric data. At step 201, air volume is segmented from patient's volumetric data using adaptive thresholding. This air volume comprises of patient's anatomical airway volume and outer air volume. Step 203 exclude the outer air volume from the volume obtained in the step 201 using morphological operations. The process of segmentation and performing themorphological operations are performed on two-dimensional sagittal slices of volumetric data. Noise components are also removed through morphological operations as in step 203.

At step 205, a number of disconnected components in each sagittal slice are calculated. At step 207, a condition is evaluated for checking the number of disconnected components in each sagittal slice. This condition follows one of the two decisions as in step 209 and step 211. If number of disconnected components is greater than four, then area of slice would be considered as zero as in step209. Similarly, if number of disconnected components are less than or equal to four, then the area of the largest disconnected component would be assigned for the slice area in the particular slice as in step 211. Eccentricity of largest disconnected component out of received disconnected component would be calculated separately for each of the sagittal slice in step 213.

The eccentricity of each disconnected component is calculated with the following formula.

$$\text{Eccentricity} = \frac{\text{Minor axis length}}{\text{Major axis length}}$$

The eccentricity value lies between values 0 to 1. At step 215, the eccentricity of each slice is checked whether it is less than or greater than 0.5. At step 217, the slice eccentricity is assigned to zero if it is less than 0.5. At step 219, slice eccentricity is assigned as received for the particular slice if it is greater than or equal to 0.5.

Figure 3:
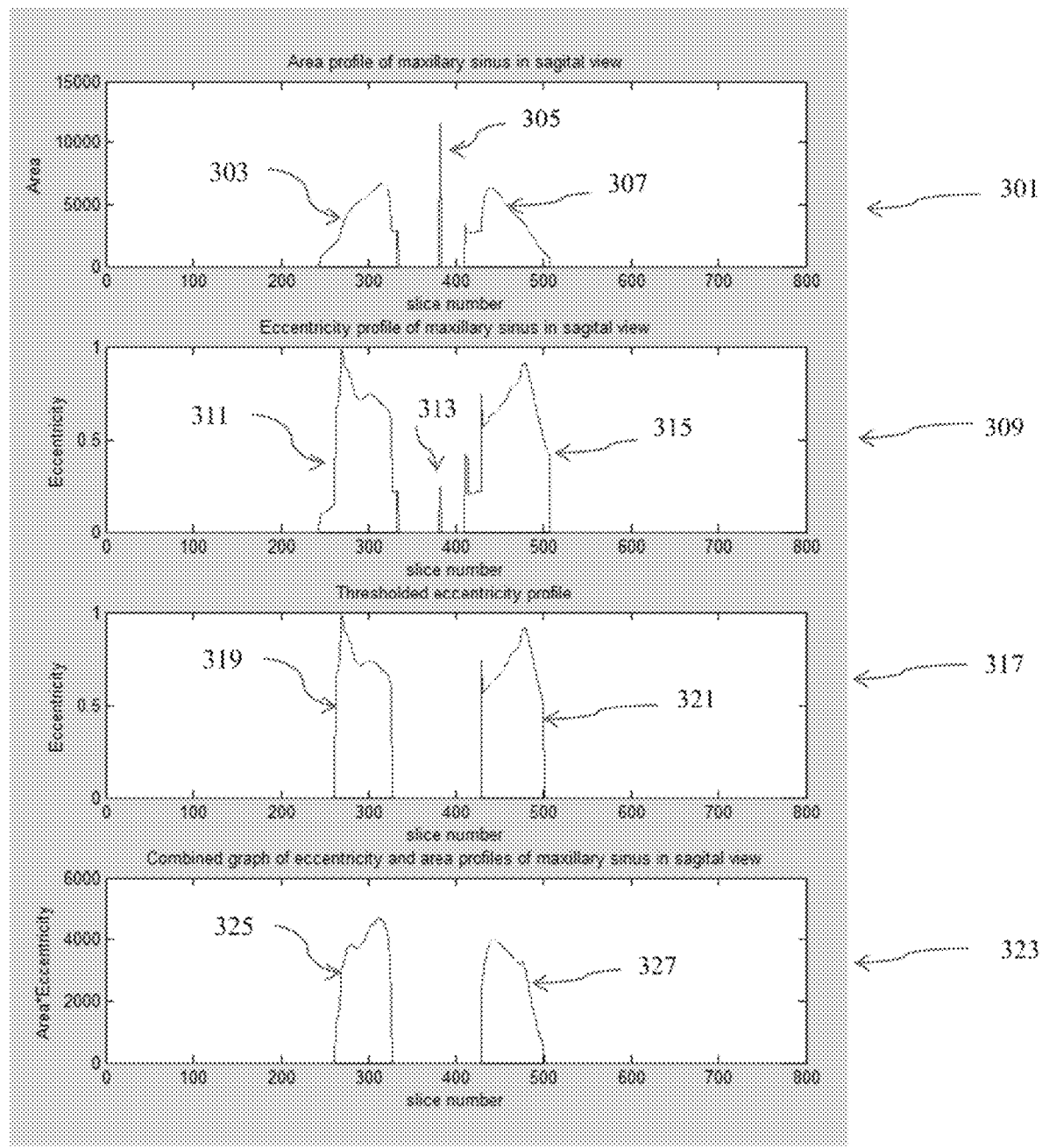
FIG. 3 illustrates the graphical profile of area and eccentricity (AE profile) of maxillary sinus as per the sagittal view of the volumetric data, in accordance with an embodiment of the present subject matter.

FIG. 3 illustrates various graphical profiles associated with area and eccentricity of maxillary sinus as per the sagittal view of the volumetric data.

At step 301, area profile is represented graphically in corresponding sequence of the sagittal slices, which comprises of three peaks represented as entities 303, 305 and 307. This profile is the representation of step 211. As per the variety of data, entities similar to 305 may and may not exist in area profile. This entity is associated with the area of pharyngeal airway in few slices. This entity is not desired in this method and has to be removed. Entity 303 and 307 are cross-sectional areas of left and right side of maxillary sinus in sagittal view. These areas have been derived from the maximum disconnected component in step 211.

Similarly, step 309 shows the eccentricity profile as of step 213. This eccentricity profile comprises of entities 311, 313 and 315. As per the variety of data, entities similar to 313 may and may not exist in eccentricity profile. This entity is associated with the eccentricity of pharyngeal airway in few slices. This entity is not desired in this method and has to be removed. Entity 311 and 315 are eccentricity profiles of left and right maxillary sinuses in sagittal view. These entities have been derived from the eccentricity of maximum disconnected component in step 213. Entity 317 is a representation of eccentricity after thresholding with 0.5 as of step 219. This entity comprises of entities 319 and 321. Both these entities are the eccentricity profiles of maxillary sinuses after thresholding. Entity 323 shows the AE profile after multiplication of area and eccentricity of each slice. This entity is comprised of the entities 325 and 327 and represents left and right profile of maxillary sinus. The level1 VOI for the segmentation is obtained using this profile.

Returning to FIG. 2, the multiplication of area (as in step 211) and eccentricity (as in step 219) of each slice is obtained in step 221. It has been shown through AE profile at entity 323. At step 223, a level 1 volume of interest (VOI) is extracted for the segmentation of various sub-regions of upper airway volume. The level 1 VOI for the pharyngeal region, nasal cavity region and para-nasal region are extracted by selecting the sagittal slices as per profile obtained at entity 323. Level 1 VOI is required for the segmentation of volume at an intermediate step, and uses as input for further segmentation of the specific sub-regional volumes of human upper airway.

FIG. 4 is comprised of example definitions to detect landmarks for the selection of ROI on the mid sagittal plane. The anterior, posterior, superior and inferior limits for selection of ROI are defined based on the anatomical knowledge of the human skull. This methodology can be used for automatic-landmark identification. The rules for classification of landmarks in the selected region are also defined in the FIG. 4.

The landmarks required for segmentation of upper respiratory tract exists in the mid sagittal plane. Automatic detection of mid sagittal plane from the volumetric data is considered as the initial step for landmark identification.

Figure 5:
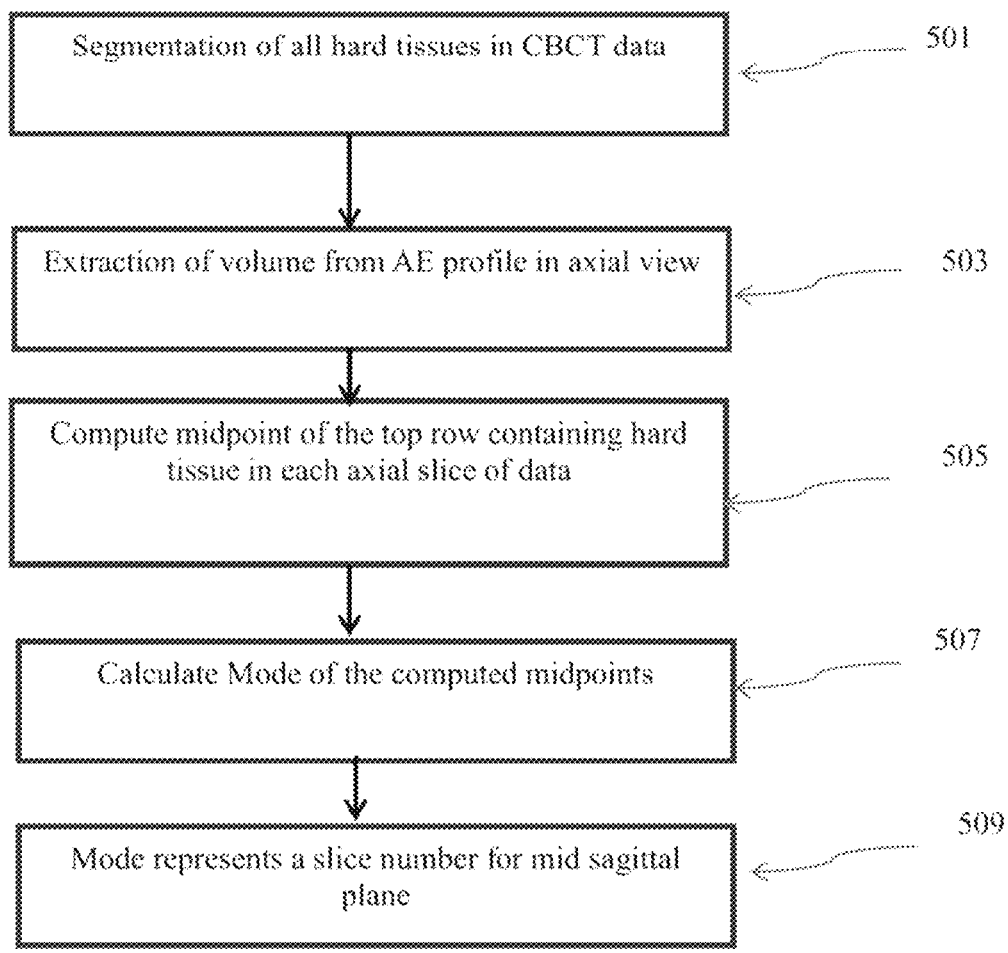
FIG. 5 illustrates a method for automatic detection of mid sagittal plane from the volumetric data, in accordance with an embodiment of the present subject matter.

FIG. 5 illustrates a method for detection of mid sagittal plane from the volumetric data. At step 501, segmentation of hard tissue from the complete volumetric data using adaptive thresholding is performed. At step 503, the level 1 VOI of the bone segmented data in the axial view is extracted based on the peaks of the AE profile. At step 505, the upper profiles of the level 1 VOI slice wise in axial view is extracted. The midpoint (column coordinates) of the top row consisting of bone in the slice is calculated, the process is performed with all the quarter data. The mode is calculated of the midpoints extracted from the quarter data in step 507. The midpoint (column coordinate) which occurs frequently from all the slices is identified by calculating the mode. Step 509 assigns the midpoint obtained from the mode as the mid sagittal slice. Using the mid sagittal slice the required landmarks are identified.

The mid sagittal slice is divided into four regions, based on the anatomical knowledge of the human skull. The boundary definition for division of mid sagittal plane into four regions is given in FIG. 4 and is based on anatomical knowledge of the human skull. Based on the anterior, posterior, superior and inferior limits the mid sagittal plane is cropped into four regions. Initial reference landmark is required to crop the mid sagittal plane into required regions. The present subject matter uses PNS (posterior nasal spine) as the reference landmark. Reference landmark (PNS) has to be detected automatically.

Figure 6:
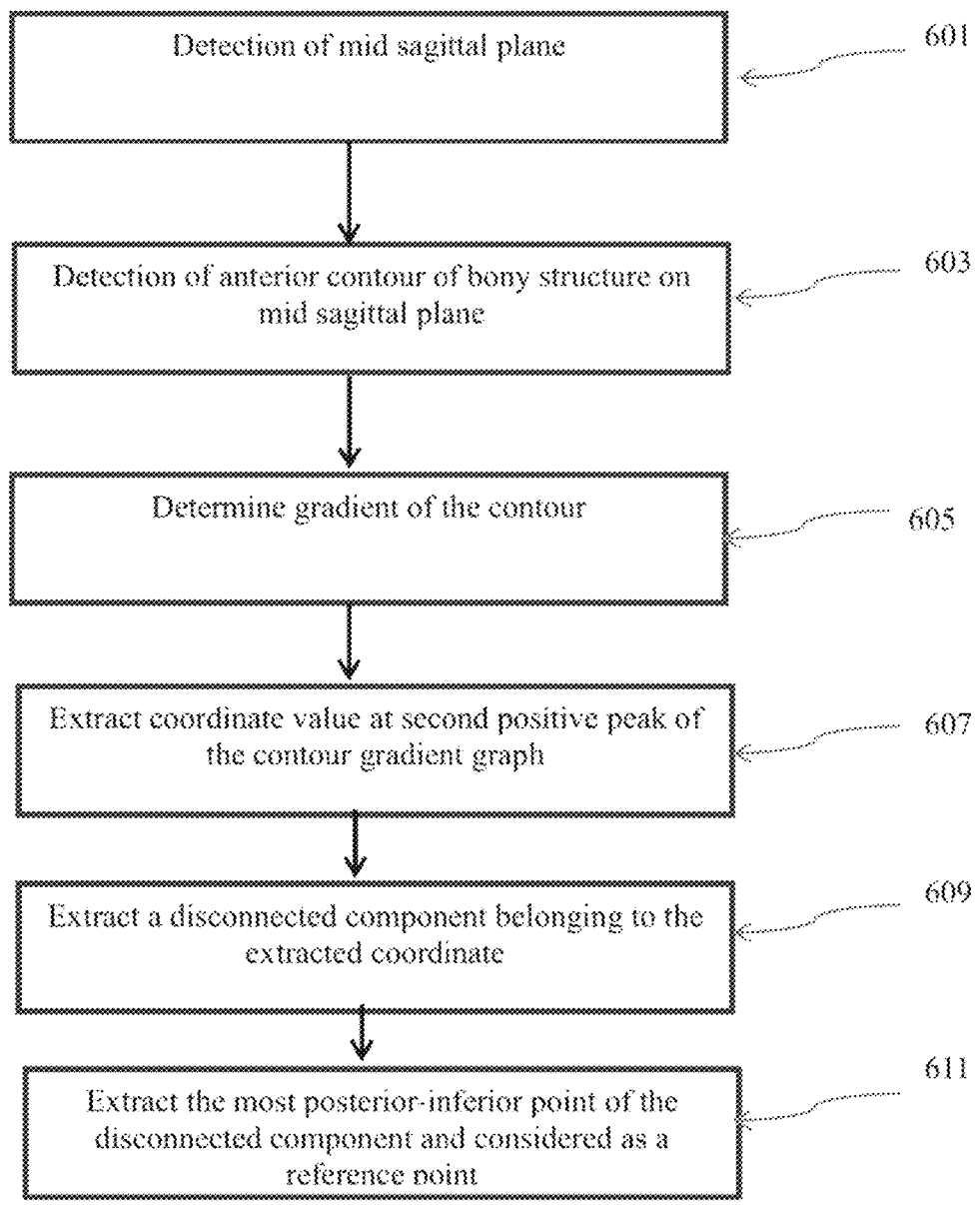
FIG. 6 illustrates a method for automatic reference landmark detection from the volumetric data, in accordance with an embodiment of the present subject matter.

FIG. 6 shows the method for automatic detection of reference landmark from the mid sagittal plane. Step 601 shows the detection of the mid sagittal plane. The mid sagittal plane is detected by using the methodology shown in FIG. 5. The bone segmented mid sagittal plane from sagittal view is detected. At step 603, most anterior placed bony points (column coordinates) on the mid sagittal plane is extracted. At step 605 the gradient of the extracted column coordinates is calculated.

Figure 7:
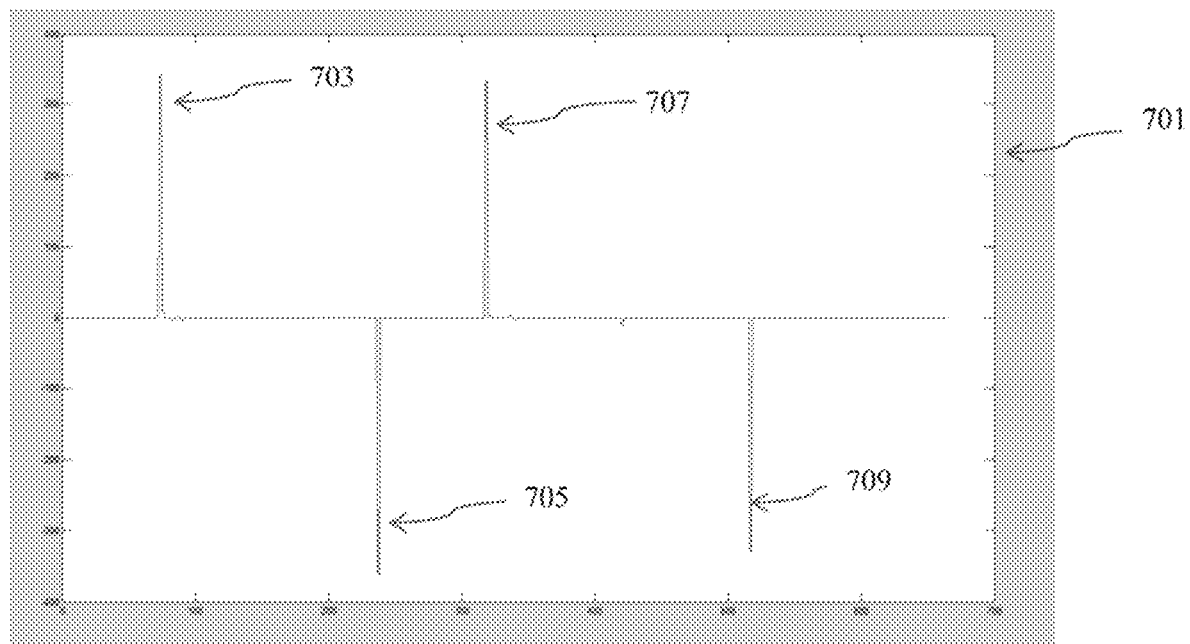
FIG. 7 illustrates the graphical representation of gradient of contour on mid sagittal plane, in accordance with an embodiment of the present subject matter.

The graphical representation of the gradient of these coordinates is given in the FIG. 7. There are existing four peaks (two negative and two positive) in the graphical representation of gradient shown as entities 703, 705, 707 and 709. These peaks represent the maximum variations in the coordinates at those instances. The entity 703, positive peak represents the start of the Nasion landmark's region. The entity 705 represents the end of the Nasion landmark's region. The entity 707, positive peak represents ANS (Anterior nasal spine) region. The entity 709 represents the end of the lower mandible region. The coordinates obtained at entity 707 is used for determination of the PNS landmark. Step 607 shows extraction of the coordinates of the second positive peak (entity 707) from the graphical representation of the gradient. Step 609 the disconnected component at the extracted coordinates of the bone segmented mid sagittal slice is considered and the rest of the slice is marked zero. Step 611 shows the extraction of most posterior-inferior point on the disconnected component.

Figure 8:
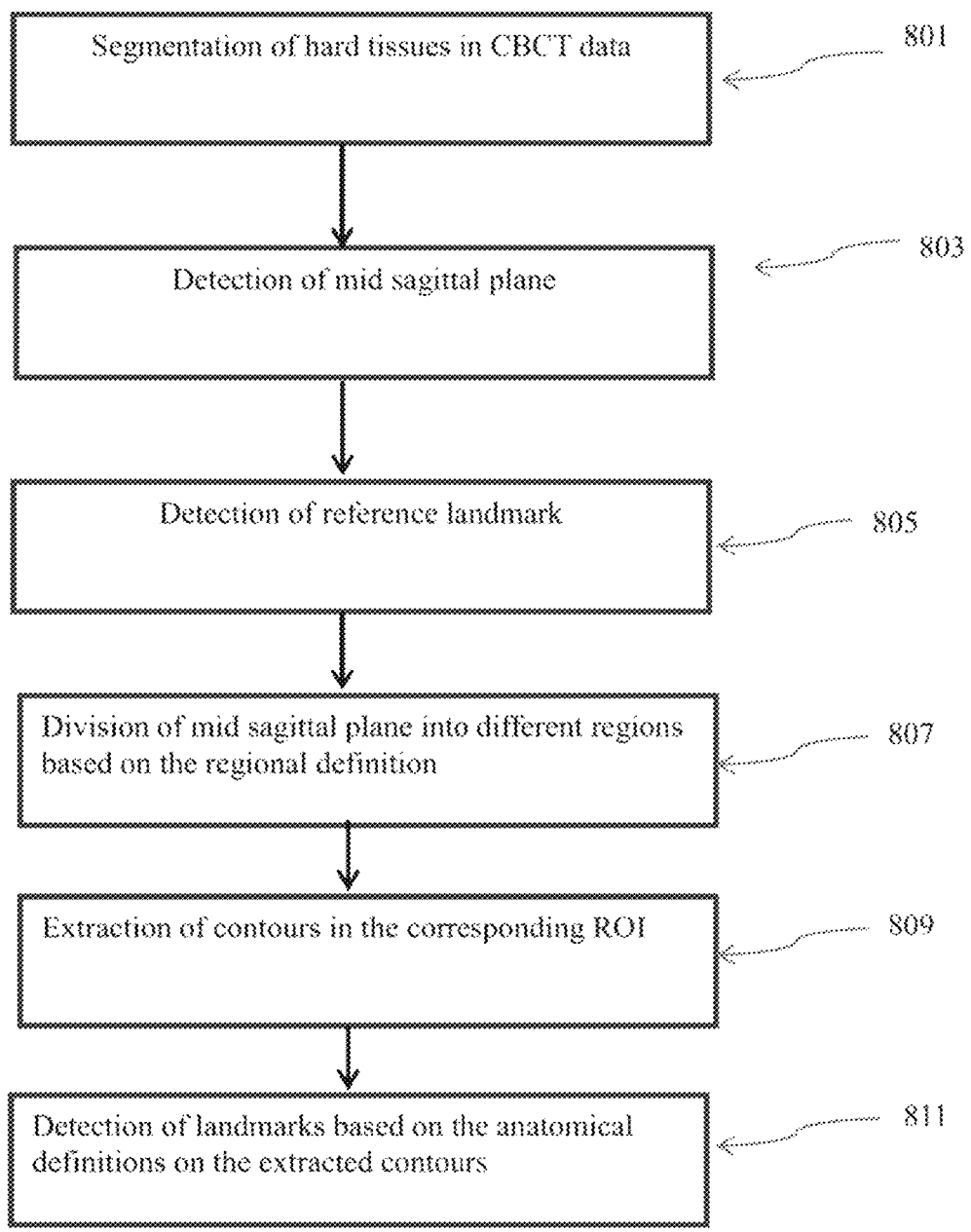
FIG. 8 illustrates a method for automatic landmark detection on skull, in accordance with an embodiment of the present subject matter

FIG. 8 illustrates the methodology for automatic landmark identification from the volumetric data. At step 801, hard tissues are segmented from the CBCT data using adaptive thresholding. Step 803 refers the method for automatic detection of mid sagittal plane. Step 805 refers the method for automatic detection of reference landmark from the mid sagittal plane. At step 807, the mid sagittal plane is cropped into four regions based on the anatomical boundary definitions given in the FIG. 4. At step 809, the bone contours are extracted in the corresponding regions. At step 811 extracted contours are further used for detection of landmarks based on their anatomical boundary definitions.

Table 1 is comprised of definitions for the selection of level2 VOI. These definitions are derived from the anatomical knowledge of various sub-regions of human airway. Similar definitions can be derived for the segmentation of other volumetric regions. These example definitions demonstrate the potential of this present subject matter for the accurate segmentation of volumetric regions in human upper airway. However, the methodology can also be used for the segmentation of other regions with the derivation of new definitions from their anatomical knowledge. Table 1 also shows the features to be extracted from the initially cropped volumes for each sub region, wherein such features are extracted based on the shape and geometric features of the organ. The constraints for classifying the sub-regions based on the extracted features are also given in the Table 1.

TABLE 1

| | | | Volume cropping criteria | | | |
|---|---|---|---|---|---|---|
| S.No | Regions | Limits | Anatomical and technical definitions for region of interest extraction | Required landmarks | Feature to be extracted | Feature classification on criteria |
| 1 | Nasopharyyx | Anterior | Line perpendicular to FH plane passing through PNS in sagittal view | 1. PNS (Posterior Nasal Spine) | Disconnected components in each sagittal slice | Disconnected component placed inferiorly in each sagittal slice joining the inferior boundary |
| | | Posterior | — | | | |
| | | Upper | — | | | |
| | | Lower | line parallel to FH plane passing through PNS, in sagittal view | | | |
| | | Lateral | Soft tissue contour of the pharyngeal lateral walls | | | |
| 2 | Oro pharynx | Anterior | Line perpendicular to FH plane passing through PNS, in sagittal view | 1. PNS (Posterior Nasal Spine) 2. C3ai (anterior inferior point of third cervical) | Disconnected components in each sagittal slice | All disconnected components in each sagittal slice |
| | | Posterior | — | | | |
| | | Upper | Line parallel to FH plane passing through PNS, in sagittal view | | | |
| | | Lower | Line parallel to FH plane passing through C3ai | | | |
| | | Lateral | Soft tissue contour of the pharyngeal lateral walls | | | |

TABLE 1-continued

| | | | Volume cropping criteria | | | |
|---|---|---|---|---|---|---|
| S.No | Regions | Limits | Anatomical and technical definitions for region of interest extraction | Required landmarks | Feature to be extracted | Feature classification on criteria |
| 3 | Hypo pharynx | Anterior | Line perpendicular to FH plane passing through PNS | 1. PNS (Posterior Nasal Spine) 2. C3ai (anterior-inferior point of third cervical) 3. C4ai (superior-posterior point of second cervical) | Disconnected components in each sagittal slice | All disconnected components in each sagittal slice |
| | | Posterior | — | | | |
| | | Upper | Line parallel to FH plane passing through C3ai | | | |
| | | Lower | Line parallel to FH plane passing through C4ai | | | |
| | | Lateral | Soft tissue contour of the pharyngeal lateral walls | | | |
| 4 | Nasal Cavity | Anterior | Soft tissue contour of the nose | 1. PNS (Posterior Nasal Spine) 2. Nasion | Calculate circularity (C) and eccentricity (E) of disconnected components in each slice of VOI | E > 0.2 and C > 0.3 |
| | | Posterior | Line perpendicular to FH plane passing through PNS | | | |
| | | Upper | Line parallel to FH plane passing through Nasion | | | |
| | | Lower | Line parallel to FH plane passing through PNS | | | |
| | | Lateral | Sagittal plane perpendicular to FH plane passing through the lateral walls of the maxillary sinus | | | |
| 5 | Frontal Sinus | Anterior | Line perpendicular to FH plane passing through Nasion | 1. PNS (Posterior Nasal Spine) 2. Nasion | Disconnected component of the slice | Disconnected component of the slice which are placed anterior inferior of the slice |
| | | Posterior | Line perpendicular to FH plane passing through PNS | | | |
| | | Upper | — | | | |
| | | Lower | Line parallel to FH plane passing through Nasion | | | |
| | | Lateral | Sagittal plane perpendicular to FH passing through the lateral walls of the maxillary sinus | | | |
| 6 | Sphenoid Sinus | Anterior | Line perpendicular to FH plane passing through PNS | 1. PNS (Posterior Nasal Spine) 2. C2sp (superior-posterior point of second cervical) | Disconnected component of the slice | Disconnected component not touching the inferior border of the slice inferior border of the slice |
| | | Posterior | Line perpendicular to FH plane passing through C2sp | | | |
| | | Upper | — | | | |
| | | Lower | Line parallel to FH plane passing through PNS | | | |
| | | Lateral | Sagittal plane perpendicular to FH plane passing through the lateral walls of the maxillary sinus | | | |
| 7 | Ethmoidal Sinus | Anterior | Line perpendicular to FH plane passing through Nasion | 1. Nasion 2. PNS (Posterior Nasal Spine) | Calculate circularity (C) and eccentricity (E) of disconnected components in each slice of VOI | ~(E > 0.2 and C > 0.3) |
| | | Posterior | Line perpendicular to FH plane passing through PNS | | | |
| | | Upper | Line parallel to FH plane passing through Nasion | | | |
| | | Lower | Line parallel to FH plane passing through PNS | | | |
| | | Lateral | Sagittal plane perpendicular to FH | | | |

TABLE 1-continued

Volume cropping criteria

| S.No | Regions | Limits | Anatomical and technical definitions for region of interest extraction | Required landmarks | Feature to be extracted | Feature classification on criteria |
|---|---|---|---|---|---|---|
| 8 | Maxillary Sinus | Anterior | plane passing through the lateral walls of the maxillary sinus Sagittal plane perpendicular to the FH plane, passing through the most anterior point of maxillary sinus | — | Generation of mask by viewing anterior, posterior, superior and inferior profiles of the maximum disconnected components of the volume | C > 0.6 for coronal slices and C > 0.5 for axial slices |
|   |   | Posterior | Sagittal plane perpendicular to the FH plane, passing through the most posterior point of maxillary sinus |   |   |   |
|   |   | Upper | Sagittal plane parallel to the FH plane, passing through the most upper point of maxillary sinus |   |   |   |
|   |   | Lower | Sagittal plane parallel to the FH plane, passing through the most lower point of maxillary sinus |   |   |   |
|   |   | Lateral | Axial plane perpendicular to the FH plane passing through lateral walls of maxillary sinus |   |   |   |

Aforesaid Table 1 illustrates example definitions for the selection of level 2 VOI derived from the domain knowledge of various sub-regions of airway.

Figure 9:
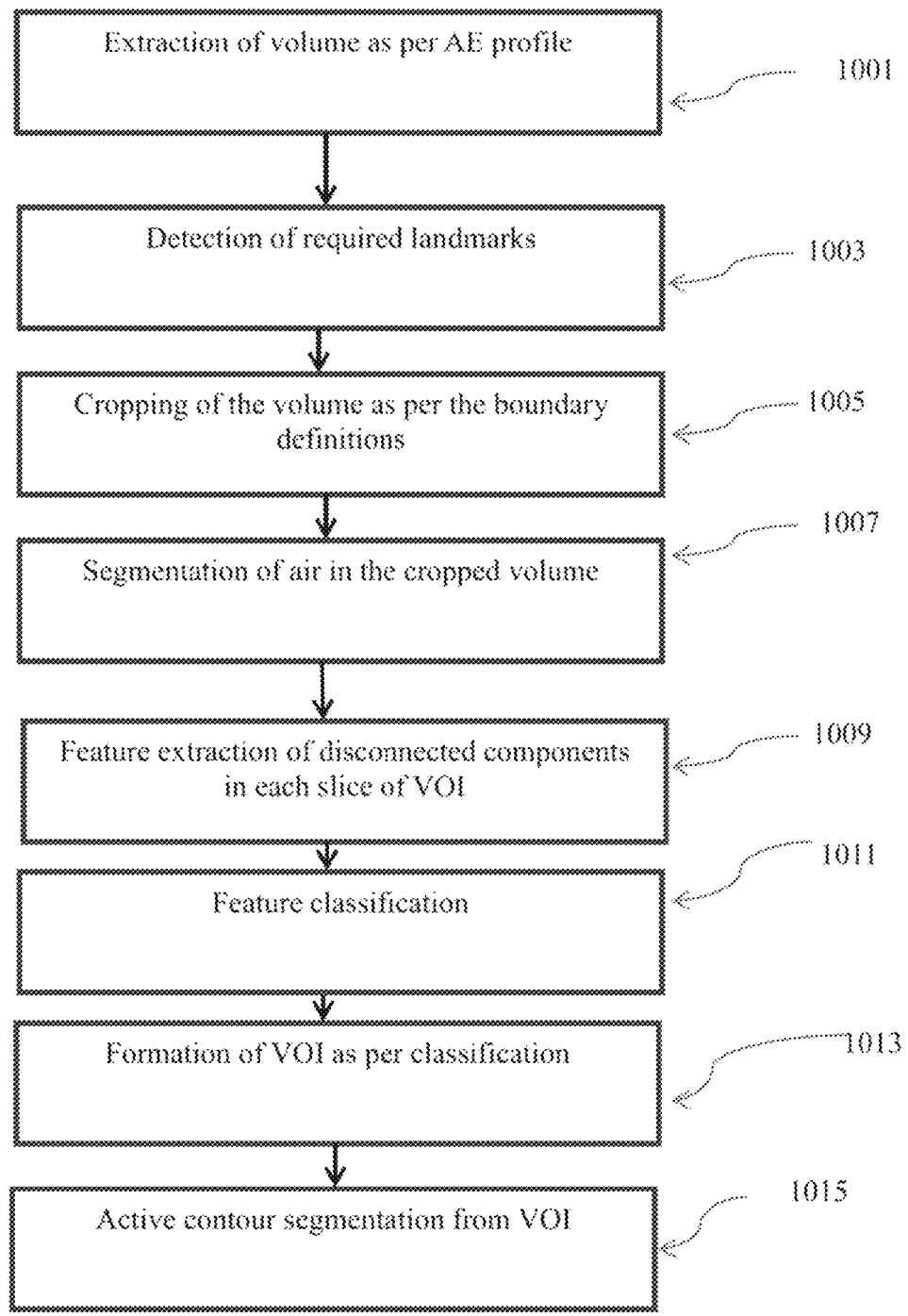
FIG. 9 illustrates a method for automatic segmentation of sub-regional volumes of human upper airway, in accordance with an embodiment of the present subject matter.
Figure 10:
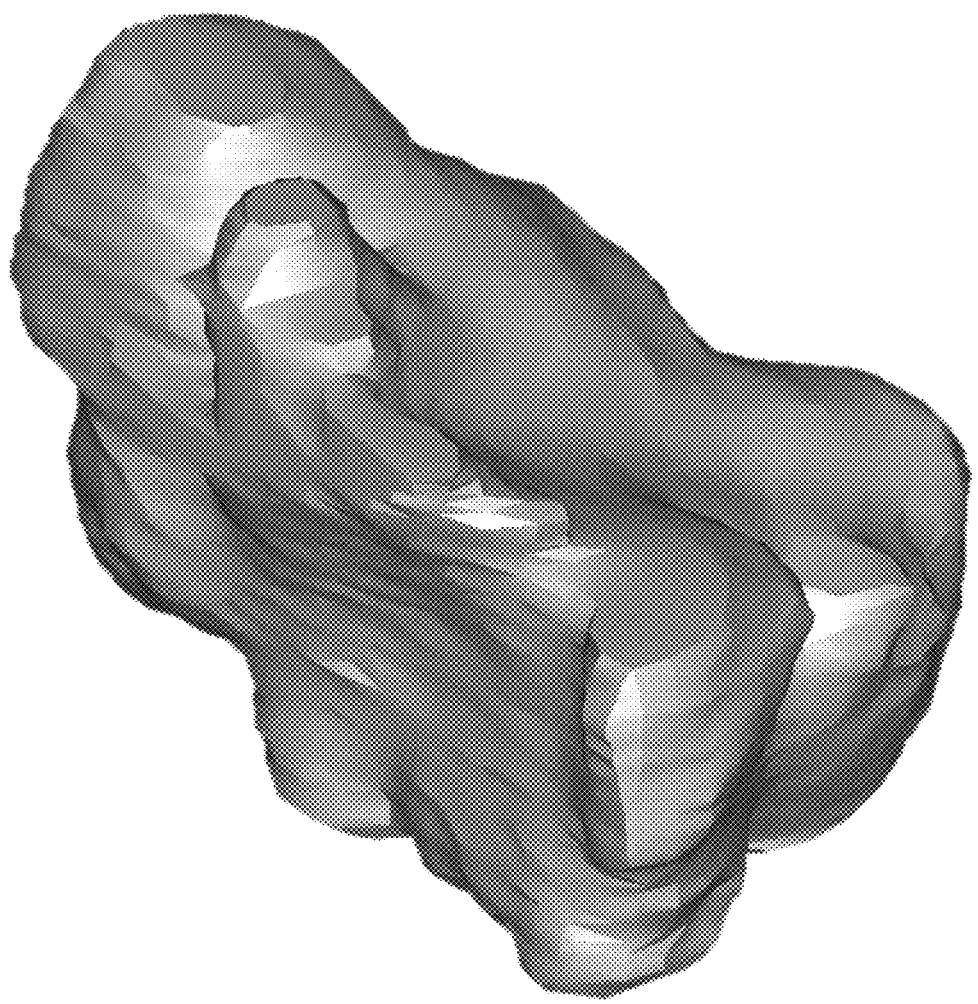
FIG. 10 illustrates an example left maxillary sinus volume segmented automatically from the volumetric data, in accordance with an embodiment of the present subject matter.
Figure 11:
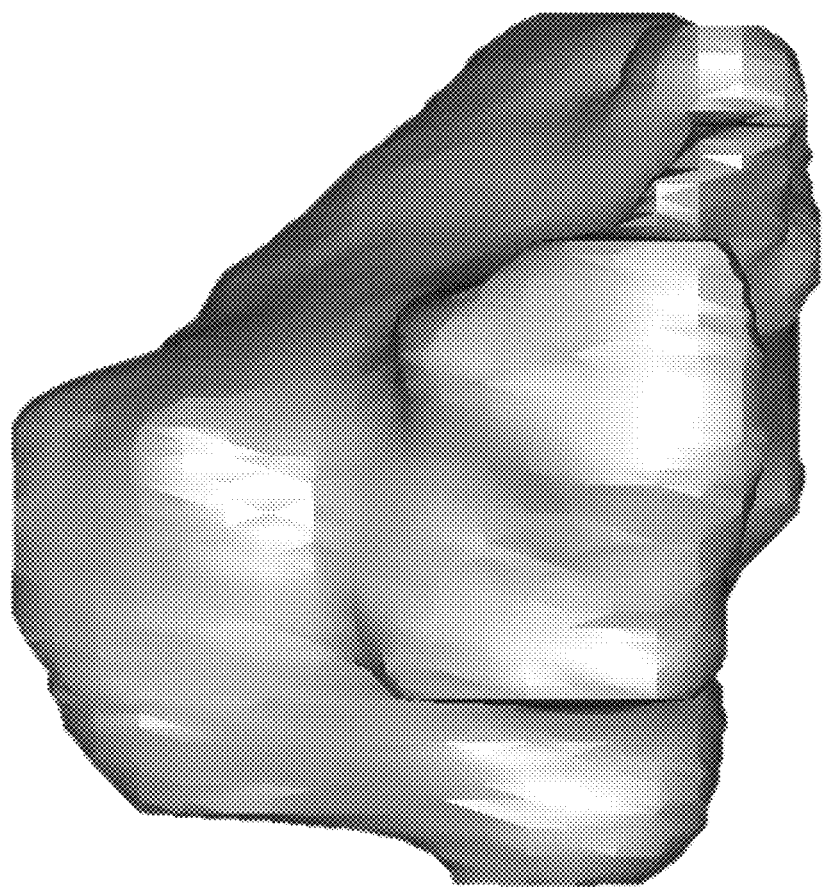
FIG. 11 illustrates an example right maxillary sinus volume segmented automatically from the volumetric data, in accordance with an embodiment of the present subject matter.
Figure 12:
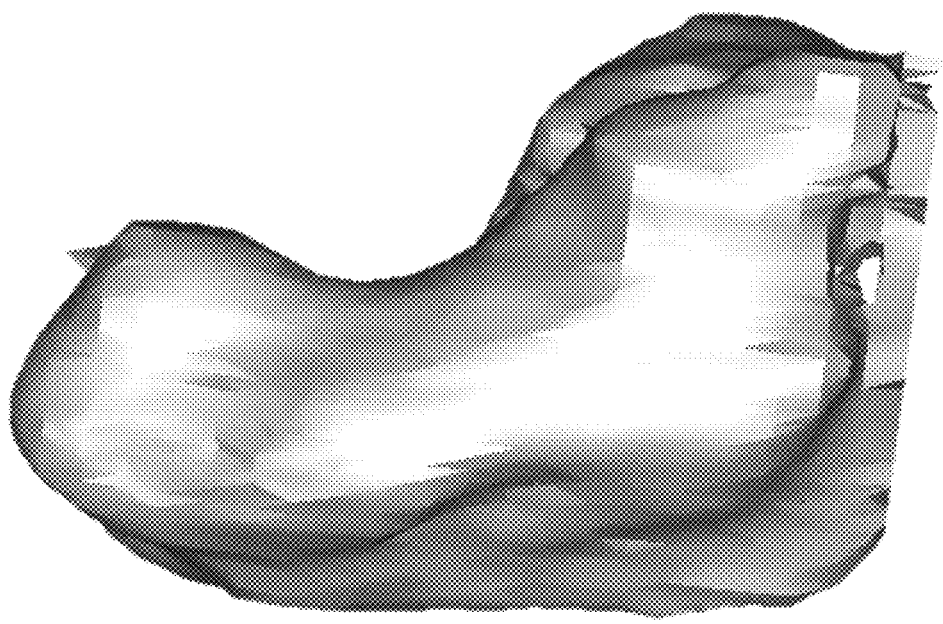
FIG. 12 illustrates an example Sphenoid sinus volume segmented automatically from the volumetric data, in accordance with an embodiment of the present subject matter.
Figure 13:
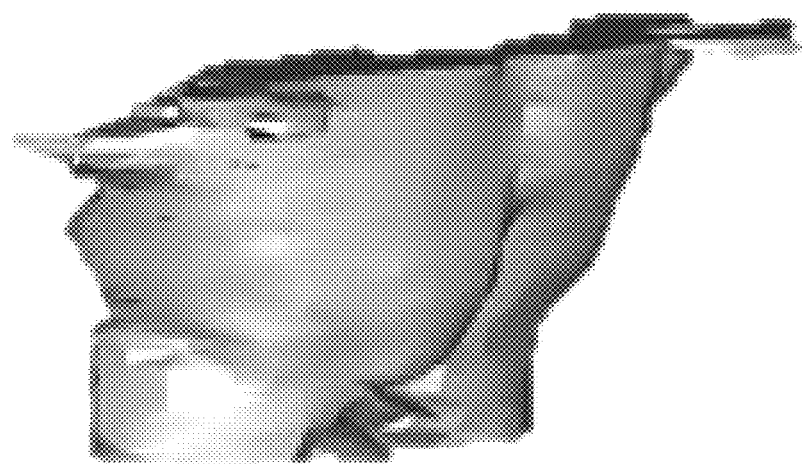
FIG. 13 illustrates an example Frontal sinus volume segmented automatically from the volumetric data, in accordance with an embodiment of the present subject matter.
Figure 14:
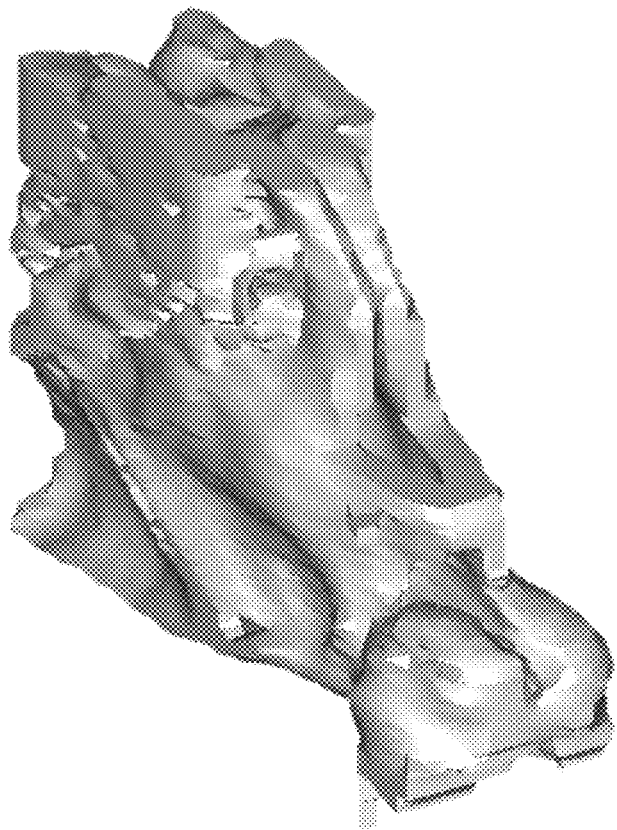
FIG. 14 illustrates an example Nasal cavity volume segmented automatically from the volumetric data, in accordance with an embodiment of the present subject matter.
Figure 15:
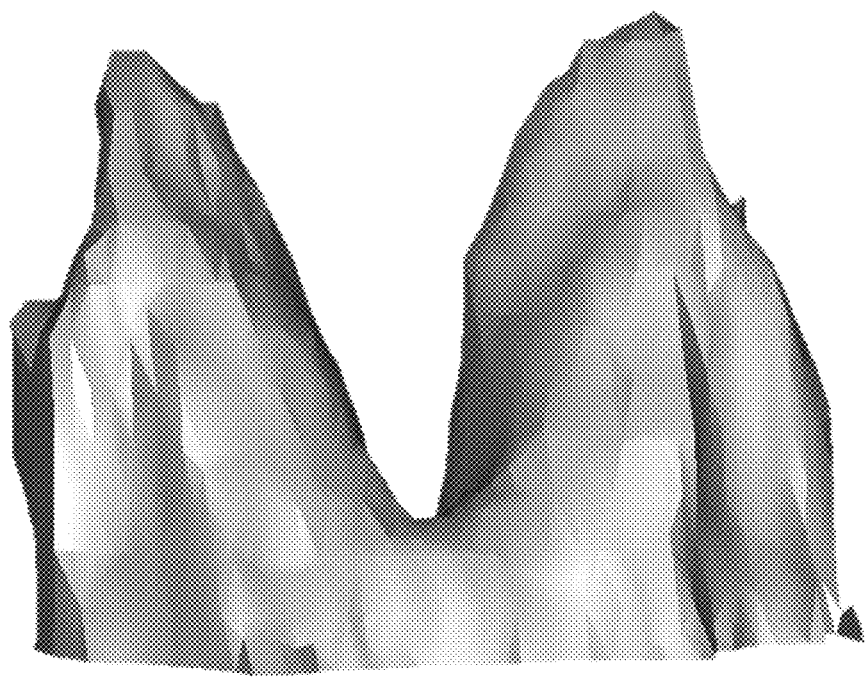
FIG. 15 illustrates an example Naso-pharyngeal volume segmented automatically from the volumetric data, in accordance with an embodiment of the present subject matter.
Figure 16:
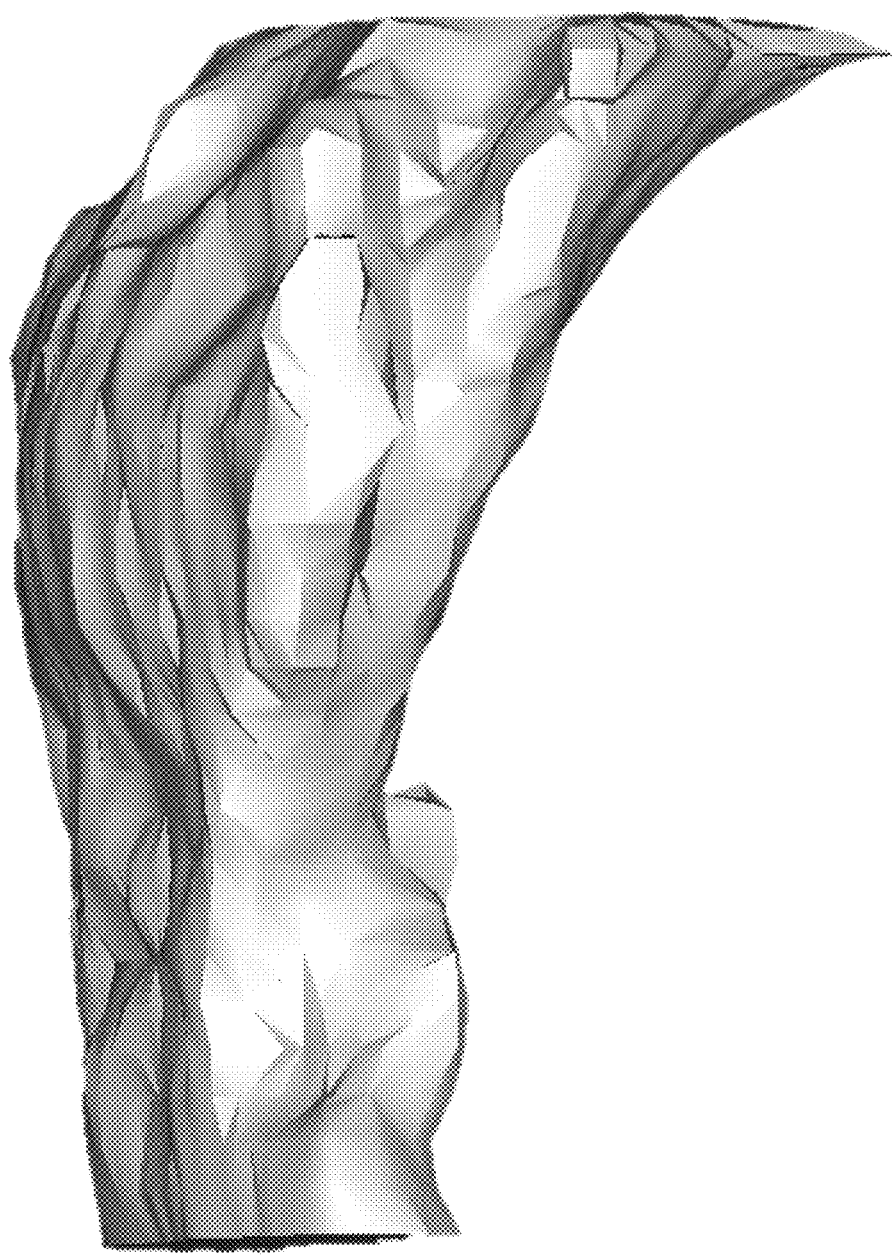
FIG. 16 illustrates an example Oro-pharyngeal volume segmented automatically from the volumetric data, in accordance with an embodiment of the present subject matter.
Figure 17:
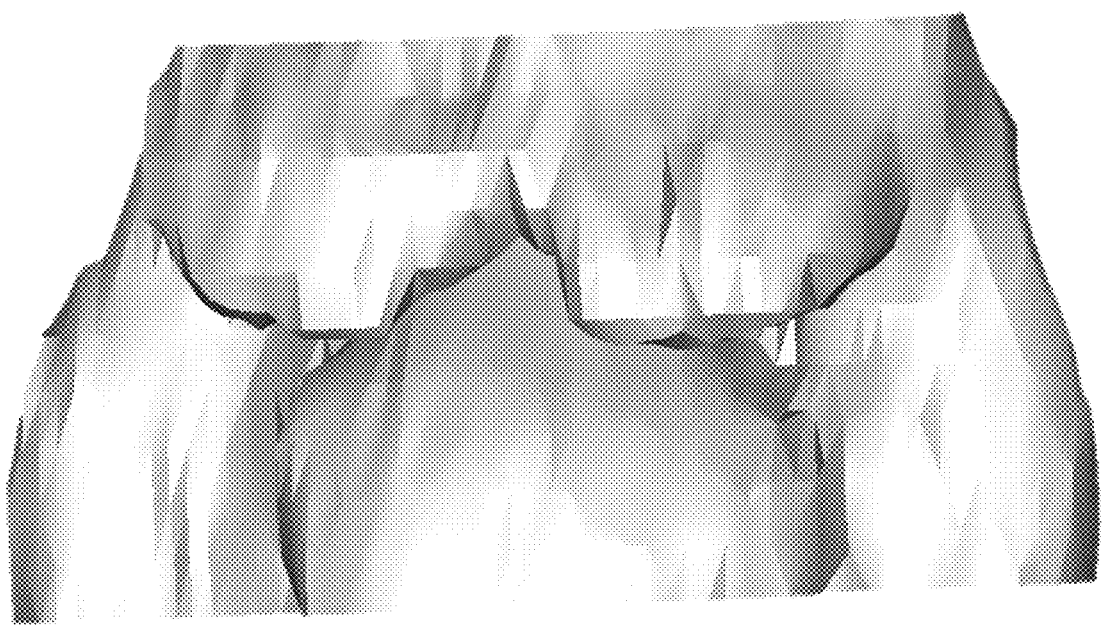
FIG. 17 illustrates an example Hypo-pharyngeal volume segmented automatically from the volumetric data, in accordance with an embodiment of the present subject matter; and Table 1 illustrates example definitions for the selection of level 2 VOI derived from the domain knowledge of various sub-regions of airway, in accordance with an embodiment of the present subject matter.

FIG. 9 illustrates a method for automatic segmentation of the sub-regional volumes (level2 VOI) of upper respiratory tract. At step 1001 the slice numbers are extracted from the AE profile in entity 323 of FIG. 3. The volume between sagittal slices of two peaks in AE profile consist the pharyngeal airway region, nasal cavity, ethmoidal, frontal, and sphenoid sinuses. At step 1003, the required landmarks for the extraction of sub-region are detected. The methodology for detection of landmarks is disclosed in the FIG. 8. At step 1005, the sub regional volumes are cropped according to the detected landmarks and the boundary definitions given in the FIG. 9. At step 1007, the air segmentation is performed based on the adaptive thresholding in the cropped regions. At step 1009, the features are extracted from the air segmented volume. The type of features to be extracted is given in Table 1 and is based on shape and geometry of the organ. At step 1011, the extracted features are classified according to the rules mentioned in the Table 1. At step 1013, the level3 VOI of the airway sub-regions could be formed as per classification. The definitions required for classification is given in Table 1. The detected level3 VOI is considered as the contour initialization in the sub-region to be segmented. At step 1015 active contour segmentation is performed based on the extracted level3 VOI and the original cropped images. The volumetric segmentation of various sub regions of the upper respiratory tract could be achieved by using the methodology shown in the FIG. 9.

The remaining figures FIGS. 10-17 illustrate left maxillary sinus volume, right maxillary sinus volume, Sphenoid sinus volume, Frontal sinus volume, Nasal cavity volume Naso-pharyngeal volume, Oro-pharyngeal volume, and Hypo-pharyngeal volume from the volumetric data, in accordance with an embodiment of the present subject matter.

Further, forthcoming paragraphs depict example-implementation of the present subject matter. Yet, said following examples are for illustration purposes only and shall not be construed to cover or reflect the full scope of present subject matter.

Detection of Nasion Landmark

This example discloses automatic detection of nasion landmark using the present methodology. The hard tissue of CBCT data is segmented using adaptive thresholding. Automatic detection of mid sagittal plane and reference landmark PNS is clearly disclosed in the methodology given in FIG. 5 and FIG. 6. The mid sagittal plane in sagittal view is cropped into four regions based on the reference landmark (PNS). The posterior limit, line perpendicular to FH plane passing through PNS, and lower limit, line parallel to FH plane passing through PNS are chosen to crop the region 1 in the mid sagittal plane. The nasion landmark exists in the region 1 mentioned in the FIG. 4. The contour is extracted by collecting all the anterior points in the region 1. The gradient of the extracted points is calculated. The graphical representation is shown in the FIG. 7. The coordinates between first positive peak and first negative peak consists of nasion landmark, the contour comprising of coordinates between these two peaks is considered for nasion landmark detection. Based on anatomical definition, the nasion landmark is the point which is placed most posteriorly in the considered contour. Therefore the most posterior point on the contour is detected as the nasion landmark. Similarly the same methodology can be used for automatic detection of other landmarks, in their corresponding regions.

Detection of Pharyngeal Airway Regions

This example discloses method for automatic segmentation of pharyngeal airway sub regions (Nasopharynx, Oropharynx and Hypopharynx). FIG. 9 illustrates a method for automatic segmentation of the sub-regional volumes of pharyngeal airway. The slice numbers are extracted for peaks of the AE profile in entity 323 of FIG. 3. The volume between sagittal slices of these peaks consist the pharyngeal region. The pharyngeal region consists of sub regions Nasopharynx, Oropharynx and Hypopharynx. Therefore the sagittal slices (level1 VOI) between these two peaks are extracted. The level 1 VOI further has to be cropped based on the definitions of the sub regions given in the Table 1. There are certain landmarks required for cropping of initial volume. Landmarks such as PNS, C3ai, C4ai are required for cropping of the pharyngeal airway region. These landmarks could be automatically detected using the methodology given in FIG. 8. The level 1 VOI is cropped based on the definitions given in Table 1 to form level 2 VOI for pharyngeal sub regions.

Nasopharynx

The landmarks required for segmentation of Nasopharynx is only PNS, which would be automatically extracted by the methodology shown in FIG. 6. The level 1 VOI is cropped based on the boundary definitions such as Anterior limit, line perpendicular to FH plane passing through PNS in sagittal view, lower limit, line parallel to FH plane passing through PNS in sagittal plane, and lateral limit, soft tissue contour of the pharyngeal wall (which could be the initial volume, extracted by using AE profile). The level2 VOI is extracted by cropping level 1 VOI using the boundary definitions. The air segmentation using adaptive thresholding is performed on the level2 VOL The different features in the air segmented volume are extracted. These features to be extracted are mentioned in the Table 1. Disconnected components in each slice of the air segmented volume are extracted for segmentation of Nasopharynx. The extracted features are further classified based on the rules mentioned in the Table 1. Disconnected component placed inferiorly in the each segmented slice or the touching the inferior border are extracted for segmentation of Nasopharynx (level3 VOI). These extracted disconnected components are treated as the automatic initialized contours and these contours are further expanded using the level set segmentation algorithm. The output of the level set segmentation algorithm gives the Naso-pharyngeal region.

Similar methodology is used for segmentation of other sub regions of the upper respiratory tract such as Oropharynx, Hypopharynx, Nasal cavity and Paranasal air-sinuses.

At least by virtue of aforesaid, the present subject matter facilitates at least following advantages.

Automatic initialization of contour for segmentation of airway sub regions

Cropping of VOI is based on the boundary definitions of the airway sub regions which reduces the search space in each stage.

The present subject matter operates based on the knowledge generated from human anatomy and searches the landmark by traversing each slice in the available three sectional planes, which gives appropriate VOI detection.

The present subject matter at least leads to time-saving in respect of the volumetric analysis of upper airway sub regions.

Overall, the present subject matter proposes a fully automatic segmentation technique that causes automatic segmentation of the anatomical volume of various sub-regions of human upper airway separately for visualization, and also computes a numeric volume for further analysis.

While specific language has been used to describe the disclosure, any limitations arising on account of the same are not intended. As would be apparent to a person in the art, various working modifications may be made to the method in order to implement the inventive concept as taught herein.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment.

The scope of embodiments is by no means limited by these specific examples. Numerous variations, whether explicitly given in the specification or not, such as differences in structure, dimension, and use of material, are possible.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component.

We claim:

1. A computer-implemented method of automatically segmenting upper airway volume and sub-regions therein based on computed tomography (CT) images, said method comprising:
  a) determining an area and eccentricity (AE) profile of a maxillary sinus as a first volume of interest (VOI), said determination based on processing an upper airway-volume segmented from the CT-image data;
  b) detecting a plurality of landmarks from a plurality of regions of a mid-sagittal plane, wherein the mid-sagittal plane is detected based on segmenting hard-tissues from the CT-image data and the plurality of regions are identified within the mid-sagittal plane based on anatomical knowledge of a human skull;
  c) creating a second VOI based on dividing the first VOI into a plurality of sub-regions of the upper airway volume, said dividing based on the detected landmarks and an anatomical knowledge of the sub-regions; and
  d) performing air-segmentation upon the second VOI and extracting a plurality of pre-defined features therefrom at least based on pre-defined shapes of one or more organs associated with upper air-volume;
  e) classifying the plurality of features in accordance with a pre-defined criteria within the second VOI of step d) to automatically initialize contours and thereby achieve a third VOI; and
  f) executing active contour segmentation based on the third VOI of step e) and the second VOI of step c) to thereby cause an automatic volumetric-segmentation of the sub-regions within the upper air volume.

2. The method as claimed in claim 1, wherein the determination of the AE profile of the maxillary sinus comprises the steps of:
  (i) performing air segmentation a living being's CT image data at least based on adaptive-thresholding;
  (ii) excluding outer air volume from the volume obtained in the step (i) at least based on morphological operations;
  (iii) calculating a number of disconnected components in each of plurality of sagittal slices pertaining to the remaining volume in step (ii);
  (iv) checking the number of disconnected components in each sagittal slice;
  (v) if a number of disconnected components is greater than four, then considering area of sagittal-slice as zero, else assigning the area of a largest disconnected component for the slice area in the particular slice;
(vi) calculating eccentricity of the largest disconnected component out of received disconnected component for each of the sagittal slice separately, said calculated eccentricity corresponding to range of about 0.5 to 1.

3. The method as claimed in claim 2, wherein the determination of the AE profile of the maxillary sinus further comprises
(vii) considering eccentricity of the sagittal slice as null if less than 0.5;
(viii) multiplying an area and eccentricity for each sagittal slice to obtain the AE profile with respect to the air-segmented volume.

4. The method as claimed in claim 1, wherein the first VOI is extracted by selecting the sagittal slices corresponding to the AE profile defined by sagittal-slices of two-peaks, said peaks enclosing a volume comprising the pharyngeal airway region, nasal cavity, ethmoidal, frontal, and sphenoid sinuses.

5. The method as claimed in claim 1, wherein the mid sagittal plane in step b) is determined based on the steps of:
(i) segmenting hard-tissue from the complete volumetric data using adaptive-thresholding;
(ii) extracting bone segmented data in axial view based on the peaks of a AE profile corresponding to the segmented hard-tissue;
(iii) extracting upper profiles of the bone segmented data slice wise in the axial-view;
(iv) calculating midpoints with respect to column-coordinates of a top row comprising the bone;
(v) calculating a mode of the midpoints to identify frequently-occurring midpoints across all the slices; and
(vi) assigning the midpoint obtained from the calculated mode and thereby causing an automatic detection of the mid sagittal slice.

6. The method as claimed in claim 1, wherein a reference-landmark is determined with respect to the mid sagittal plane based on the steps of:
(i) detecting bone segmented mid sagittal plane from the sagittal view;
(ii) extracting column-coordinates with respect to extreme anterior placed bony-points at the mid sagittal plane;
(iii) calculating a gradient of the extracted column coordinates as a graphical-representation;
(iv) identifying coordinates in the graphical representation corresponding to at-least four peaks of the gradient as a) start of the Nasion landmark's region, b) end of the Nasion landmark's region, c) ANS (Anterior nasal spine) region, and d) end of the lower mandible region;
(v) extracting coordinates of a second positive peak with respect to the ANS from the graphical representation of the gradient;
(vi) considering disconnected component at the extracted coordinates of the bone segmented mid sagittal slice and ignoring rest of the slice; and
(vii) extracting an extreme posterior-inferior point on the disconnected component for automatically determining a reference-landmark as PNS.

7. The method as claimed in claim 6, wherein the mid-sagittal place is divided into a plurality of regions of interest (ROI) based on:
(i) defining anterior, posterior, superior and inferior limits for selection of the ROI based on the anatomical knowledge of the human skull;
(ii) the reference-landmark.

8. The method as claimed in claim 1, wherein the plurality of landmarks are detected from a plurality of regions of the mid-sagittal plane based on one or more of: (i) dividing the mid sagittal plane into the plurality of ROI; (ii) extracting bone-contours in the plurality of ROI; (iii) detecting landmarks based on anatomical boundary definitions.

9. The method as claimed in claim 1, wherein the pre-defined criteria in step e) for classifying the plurality of extracted features is derived from the anatomical knowledge of various sub-regions of the human airway.

10. A system for automatically segmenting upper airway volume and sub-regions therein based on computed tomography (CT) images, said system comprising:
a CT imaging system having an imager that images the anatomical airways of a living being to acquire image data; and
a processor configured to:
a) determining an area and eccentricity (AE) profile of a maxillary sinus as a first volume of interest (VOI), said determination based on processing an upper airway-volume segmented from the CT-image data;
b) detecting a plurality of landmarks from a plurality of regions of a mid-sagittal plane, wherein the mid-sagittal plane is detected based on segmenting hard-tissues from the CT-image data and the plurality of regions are identified within the mid-sagittal plane based on anatomical knowledge of a human skull;
c) creating a second VOI based on dividing the first VOI into a plurality of sub-regions of the upper airway volume, said dividing based on the detected landmarks and an anatomical knowledge of the sub-regions; and
d) performing air-segmentation upon the second VOI and extracting a plurality of pre-defined features therefrom at least based on pre-defined shapes of one or more organs associated with upper air-volume;
e) classifying the plurality of features in accordance with a pre-defined criteria within the second VOI of step d) to automatically initialize contours and thereby achieve a third VOI; and
f) executing active contour segmentation based on the third VOI of step e) and the second VOI of step c) to thereby cause an automatic volumetric-segmentation of the sub-regions within the upper air volume.

11. The system as claimed in claim 10, wherein for the determination of the AE profile of the maxillary sinus, the processor is configured to execute the steps of:
(i) performing air segmentation a living being's CT image data at least based on adaptive-thresholding;
(ii) excluding outer air volume from the volume obtained in the step (i) at least based on morphological operations;
(iii) calculating a number of disconnected components in each of plurality of sagittal slices pertaining to the remaining volume in step (ii);
(iv) checking the number of disconnected components in each sagittal slice;
(v) if a number of disconnected components is greater than four, then considering area of sagittal-slice as zero, else assigning the area of a largest disconnected component for the slice area in the particular slice;
(vi) calculating eccentricity of the largest disconnected component out of received disconnected component for each of the sagittal slice separately, said calculated eccentricity corresponding to range of about 0.5 to 1.

12. The system as claimed in claim 11, wherein for determining the AE profile, the processor is configured to execute the steps of:
(vii) considering eccentricity of the sagittal slice as null if less than 0.5;
(viii) multiplying an area and eccentricity for each sagittal slice to obtain the AE profile with respect to the air-segmented volume.

13. The system as claimed in claim 10, wherein the first VOI is extracted by the processor by:
selecting the sagittal slices corresponding to the AE profile defined by sagittal-slices of two-peaks, said peaks enclosing a volume comprising the pharyngeal airway region, nasal cavity, ethmoidal, frontal, and sphenoid sinuses.

14. The system as claimed in claim 10, wherein the mid sagittal plane in step b) is determined by the processor based on the steps of:
(i) segmenting hard-tissue from the complete volumetric data using adaptive-thresholding;
(ii) extracting bone segmented data in axial view based on the peaks of a AE profile corresponding to the segmented hard-tissue;
(iii) extracting upper profiles of the bone segmented data slice wise in the axial-view;
(iv) calculating midpoints with respect to column-coordinates of a top row comprising the bone;
(v) calculating a mode of the midpoints to identify frequently-occurring midpoints across all the slices; and
(vi) assigning the midpoint obtained from the calculated mode and thereby causing an automatic detection of the mid sagittal slice.

15. The system as claimed in claim 10, wherein the processor determines a reference-landmark with respect to the mid sagittal plane based on the steps of:
(i) detecting bone segmented mid sagittal plane from the sagittal view;
(ii) extracting column-coordinates with respect to extreme anterior placed bony-points at the mid sagittal plane;
(iii) calculating a gradient of the extracted column coordinates as a graphical-representation;
(iv) identifying coordinates in the graphical representation corresponding to at-least four peaks of the gradient as a) start of the Nasion landmark's region, b) end of the Nasion landmark's region, c) ANS (Anterior nasal spine) region, and d) end of the lower mandible region;
(v) extracting coordinates of a second positive peak with respect to the ANS from the graphical representation of the gradient;
(vi) considering disconnected component at the extracted coordinates of the bone segmented mid sagittal slice and ignoring rest of the slice; and
(vii) extracting an extreme posterior-inferior point on the disconnected component for automatically determining a reference-landmark as PNS.

16. The system as claimed in claim 15, wherein the mid-sagittal place is divided by the processor into a plurality of regions of interest (ROI) based on:
(i) defining anterior, posterior, superior and inferior limits for selection of the ROI based on the anatomical knowledge of the human skull;
(ii) the reference-landmark.

17. The system as claimed in claim 10, wherein the plurality of landmarks are detected from a plurality of regions of the mid-sagittal plane by the processor through execution of one or more of: (i) dividing the mid sagittal plane into the plurality of ROI; (ii) extracting bone-contours in the plurality of ROI; (iii) detecting landmarks based on anatomical boundary definitions.

18. The system as claimed in claim 10, wherein the pre-defined criteria in step e) for classifying the plurality of extracted features is derived by the processor from the anatomical knowledge of various sub-regions of the human airway.

* * * * *